United States Patent [19]

Gold et al.

[11] Patent Number: 4,468,400

[45] Date of Patent: Aug. 28, 1984

[54] ANTIULCER TRICYCLIC IMIDAZO [1,2-A]PYRIDINES

[75] Inventors: Elijah H. Gold, West Orange; James J. Kaminski, Long Valley; Chester Puchalski, Dover, all of N.J.

[73] Assignee: Schering Corporation, Kenilworth, N.J.

[21] Appl. No.: 450,862

[22] Filed: Dec. 20, 1982

[51] Int. Cl.³ .................. A61K 31/47; C07D 471/04; C07D 471/14; C07D 491/052
[52] U.S. Cl. .................................. 424/256; 424/258; 546/82; 546/83; 546/84; 546/121; 546/141; 546/148
[58] Field of Search .............................. 546/82, 83, 84; 424/256, 258

[56] References Cited

PUBLICATIONS

Derwent Abstract of Belgian Patent 857,008, 1/20/78.

Primary Examiner—Richard A. Schwartz
Attorney, Agent, or Firm—Gerald S. Rosen

[57] ABSTRACT

There are disclosed certain substituted tricyclic imidazo[1,2-a]pyridines which are useful in the treatment of peptic ulcer diseases.

17 Claims, No Drawings

ANTIULCER TRICYCLIC IMIDAZO[1,2-A]PYRIDINES

SUMMARY OF THE INVENTION

This invention relates to certain substituted tricyclic imidazo[1,2-a]pyridine compounds, pharmaceutical compositions thereof, novel processes and intermediates for making said compounds, and methods of treating peptic ulcer disease utilizing said compounds.

More particularly, this invention relates to a substituted imidazo[1,2-a]pyridine having a non-aromatic carbocyclic or non-aromatic heterocyclic ring fused to the pyridine represented by the formula

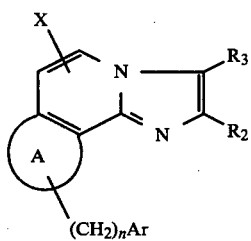

and the pharmaceutically acceptable salts thereof; wherein $R_2$ represents hydrogen, lower alkyl, or hydroxyloweralkyl;

$R_3$ represents hydrogen, lower alkyl, —$CH_2CN$, hydroxyloweralkyl, —NO, —$CH_2NC$ or

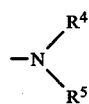

(wherein $R_4$ and $R_5$ are independently selected from the group consisting of hydrogen and lower alkyl);

X represents hydrogen, lower alkyl, halogen, hydroxy, lower alkoxy or trifluoromethyl;

A is a nonaromatic ring fused to the pyridine ring containing, with the carbon atoms of the pyridine ring to which it is attached, 5 or 6 ring atoms of which all are carbons or one is selected from nitrogen, sulfur or oxygen and the remaining atoms are carbon;

Ar represents phenyl, pyridyl, thienyl, imidazolyl, furanyl or X'-, Y'- and Z'- substituted phenyl wherein each of X'-, Y'- and Z'- independently is as hereinabove defined for X; and n is zero, one or two.

As employed throughout this specification, the term "halogen" refers to fluoro, chloro, bromo and iodo, with chloro and fluoro being preferred. The term "lower alkyl", means straight and branched-chain radicals having up to 6 carbon atoms, e.g., methyl, ethyl, propyl, butyl, t-butyl, isopropyl, neopentyl, dimethylbutyl and the like. Methyl is the preferred lower alkyl and is especially preferred at $R_2$ in Formula I.

The radical

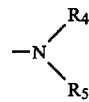

is most preferably —$NH_2$.

"Pyridyl" includes the 2-, 3-, and 4-isomers and their halogen-and lower alkyl-substituted analogs; "thienyl" includes the 2-, and 3-isomers and their halogen-and lower alkylsubstituted analogs; "imidazolyl" includes the 2- and 4-isomers, and their halogen-and lower alkyl substituted analogs. When the moiety "Ar" is the X'-, Y'-, Z'- substituted phenyl radical, it is preferred that the substituents be halogen which may be in the ortho, meta and/or para positions of the phenyl group. In those compounds in which the X-substituent is other than hydrogen, it may be at either or both the 5- or 6-positions of the imidazo[1,2-a]pyridine nucleus. When $R_4$ and $R_5$ are other than hydrogen, it is preferred that they be methyl or ethyl.

"Non-aromatic ring" includes non-aromatic rings containing 5 or 6 ring atoms which are either all carbon or one atom is sulfur, oxygen or nitrogen, and which contain zero or one double bond in addition to that at the fused position, such as cyclopentano, cyclopenteno, cyclohexano, cyclohexeno, dihydropyrano, pyrrolino, dihydrofurano, dihydropyridino, dihydrothieno and dihydrothiopyrano. The preferred ring is dihydropyrano. The hetero atom of the non-aromatic ring can be at the 7 or 9 positions in the case of a 5 membered ring and at the 10 position in the case of a six membered ring.

The —$(CH_2)_n$ Ar substituent can be on any nuclear carbon of the non-aromatic ring, preferably at the 8-position of a 5 membered ring or the 9-position of a 6 membered ring.

"Pharmaceutically acceptable salts" are acid addition salts wherein an acidic hydrogen forms an acid addition salt with an amine, e.g., the phosphate salt of the 3-amino-substituted compound.

Suitable acids for the pharmaceutically acceptable acid addition salts include hydrochloric, sulfuric, phosphoric, nitric, acetic, propionic, maleic, ascorbic, citric and the like.

The acid addition salts are prepared via procedures well known in the art, e.g. treatment with an acid such as hydrochloric acid in ether.

The compounds of this invention have an asymmetric carbon and all optically active forms are contemplated, i.e. the D or L optical isomer or the racemic mixture. The racemic mixture can be resolved by conventional means such as by use of an optically active acid to separate the D and L forms.

A preferred subgroup of compounds of Formula I are those wherein ring A is dihydropyrano and $R_2$ represents hydrogen, lower alkyl with 1 to 3 carbon atoms or —$CH_2OH$;

$R_3$ represents hydrogen, lower alkyl with 1 to 3 carbon atoms, —$CH_2OH$, —$CH_2CN$ or —$NH_2$;

X represents hydrogen or methyl; and n is zero or one.

A more preferred subgroup of compounds of the preferred subgroup of Formula I are those wherein the A ring is dihydropyrano substituted at the 9-position with phenyl.

The most preferred compounds of Formula I are those wherein ring A is dihydropyrano, $R_2$ represents —$CH_3$; and $R_3$ represents —$CH_3$, —$CH_2CN$, or —$NH_2$; X represents hydrogen; and phenyl is at the 9-position.

Examples of compounds within the scope of this invention are:

1. 2-methyl-9-phenyl-7H-8,9-dihydropyrano[2,3-c]imidazo-[1,2-a]pyridine-3-acetonitrile represented by the structure

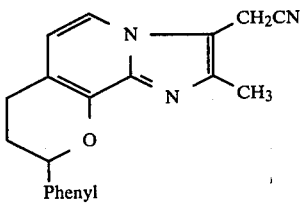

2. 3-Amino-2-methyl-9-phenyl-7H-8,9-dihydropyrano[2,3-c]-imidazo[1,2-a]pyridine represented by the structure

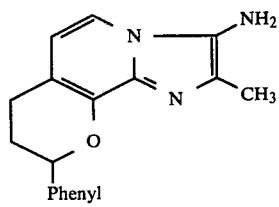

3. 2,3-Dimethyl-9-phenyl-7,8-dihydroimidazo[2,1-a]-isoquinoline represented by the structure

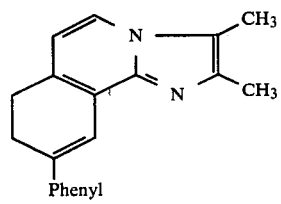

4. 3-Amino-2-methyl-9-phenyl-7,8,9,10-tetrahydroimidazo-[2,1-a]isoquinoline represented by the structure

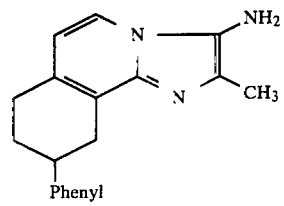

and 5. 2-Methyl-9-phenylmethyl-7,8-dihydroimidazo[2,1-a]-isoquinoline-3-acetonitrile represented by the structure

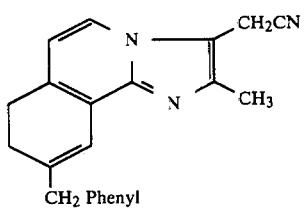

DETAILED DESCRIPTION OF THE INVENTION

The compounds of this invention can be prepared by known methods using as starting materials either known compounds or compounds which can be made by conventional means.

For example, compounds of formula I in which ring A is carbocyclic with 6 carbons, e.g. compounds 3, 4 and 5 above, can be prepared by reacting 5,6,7,8-tetrahydroisoquinolin-7-one with $Ar(CH_2)_nLi$ or Grignard to introduce the $-(CH_2)_nAr$ substituent to the ring. Dehydration of the resulting product results in the intermediate 5,6-dihydro-7-substituted isoquinoline which, upon subjection to catalytic hydrogenation, is converted to the intermediate 5,6,7,8-tetrahydro-7-substituted isoquinoline. The starting material 5,6,7,8-tetrahydroisoquinolin-7-one can be prepared following Boger, et al. J. Org. Chem., 46 2179 (1981).

The above described reactions are shown in the following Reaction Scheme I:

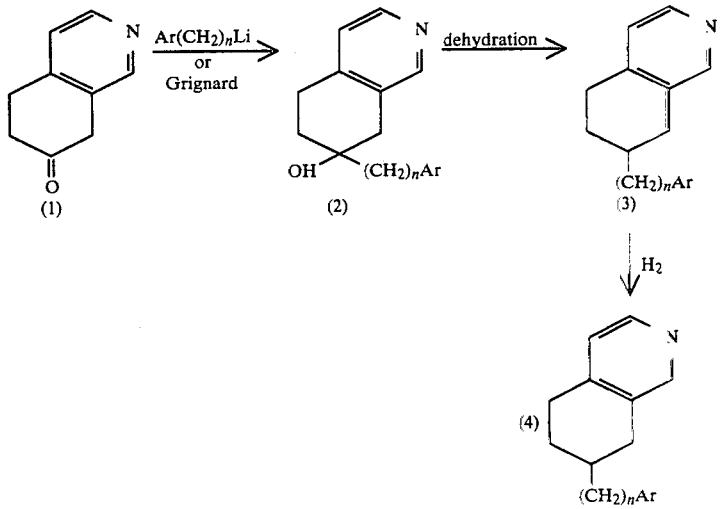

Ar and n are as defined for formula I.

Compounds (3) or (4) are converted to compounds of formula I by first reacting with sodamide to produce 1-amino-5,6,7,8-tetrahydro (or 5,6-dihydro)-7-substituted isoquinoline which can then be condensed with bromobutanone to give 2,3-dimethyl-9-phenyl-7,8,9,10-tetrahydro (or 7,8-dihydro)-imidazo[2,1-a]isoquinoline.

A compound with a hydrogen at the 3-position and a methyl at the 2-position can be prepared by using as the carbonyl reactant, chloroacetone. A compound with a 2-methyl-3-carboethoxy substituent can be prepared by using as the carbonyl reactant ethyl-2-chloroacetoacetate.

position and how alkyl can be introduced to the 2-position are equally applicable for the introduction of other substituents at those positions by using reactants which are analogously substituted.

Compounds of formula I wherein the A ring contains 5 carbon atoms can be prepared using the analogously substituted starting materials in the above described reactions.

The compounds of formula I in which the heteroatom in the A ring is oxygen, e.g. the dihydropyrano compounds can be prepared using methods described by von Standtmann, et al, J. Heterocyclic Chem. 7, 1311 (1970) as depicted in the following reaction scheme II

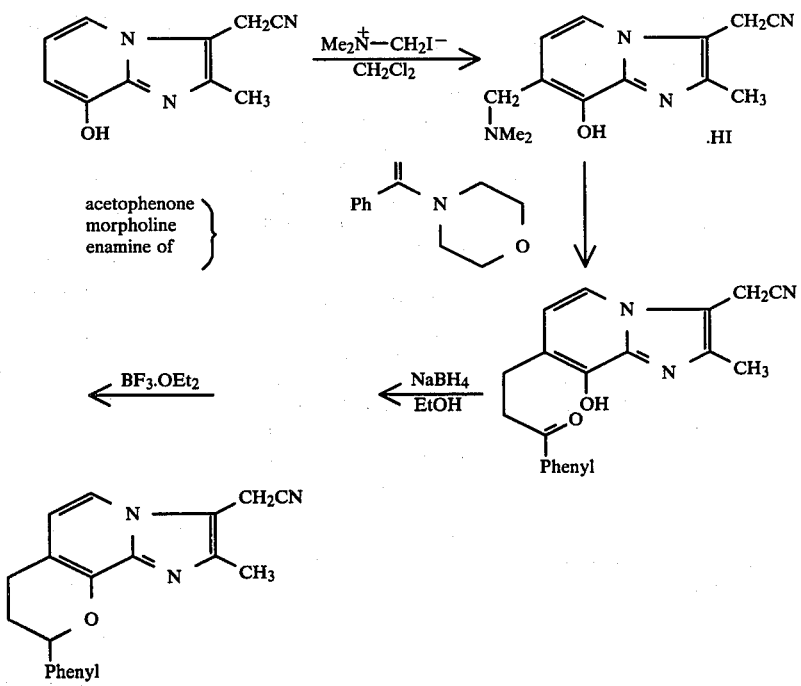

Various 3-substituted derivatives of the compounds of this invention can be prepared from the 3-hydrogen or 3-carboethoxy derivative by conventional procedures. For example, the 3-hydrogen compound can be converted to the 3-nitro derivative using a mixture of sulfuric and nitric acids. The 3-nitro derivative can then be reduced to the corresponding 3-amino compound. Alternatively, the 3-hydrogen compound can be nitrosated to the corresponding 3-nitrose compound using sodium nitrite in hydrochloric acid solution or an alkyl nitrite, e.g. n-butyl nitrite. The 3-amino derivative can be produced by reduction of the 3-nitroso derivative, e.g., with zinc and acetic acid.

The 3-carboalkoxy compounds can be converted to the corresponding 3-hydroxymethyl derivative by reaction with lithium aluminum hydride in tetrahydrofuran.

The 3-hydroxymethyl derivative, upon reaction with phosphorous oxychloride is converted to the 3-chloromethyl derivative. This latter derivative, upon reaction with an alkali metal cyanide, e.g. sodium cyanide, in a suitable solvent such as dimethylsulfoxide (DMSO), ethanol or dimethylformamide (DMF) gives the corresponding 3-cyanomethyl derivative.

The above reactions, while described to show how hydrogen, alkyl, carboalkoxy, nitro, nitroso, amino, hydroxymethyl, chloromethyl and cyanomethyl-(acetonitrile) substituents can be introduced to the 3-

The compounds of this invention are useful in the treatment of peptic ulcers. They display chemotherapeutic activity which enables them to relieve the symptoms of peptic ulcer disease, including stress ulceration, and promote healing of gastric and/or duodenal ulcers. The antiulcer activity of the compounds of this invention is identified by tests which measure their cytoprotective effect (also referred to as mucoprotective effect) and antisecretory effect in rats. The compounds are also useful as conjunctive therapeutic agents for coadministration with such anti-inflammatory/analgesic agents as aspirin, indomethacin, phenylbutazone, ibuprofen, naproxen, tolmetin and other agents having the untoward side effect of contributing irritation and damage to the gastrointestinal tract.

The compounds of this invention are evaluated for their activity characteristics by standard biological testing procedures.

In the testing procedures they are evaluated on an absolute basis and on a comparative basis with compounds known to possess the activity useful for the treatment and/or prevention of peptic ulcer disease and drug induced gastric ulceration. Such tests include testing for antisecretory effects in rats with pyloric ligation techniques. The test compounds are administered either intraperitoneally or orally in appropriate and well-defined and well-known vehicles.

In cytoprotective tests in rats in which ethanol is employed to induce gastrointestinal damage, the compounds of this invention are found to be effective for the oral treatment of the ulcerative disease states mentioned herein.

Orally, the compounds are effective at doses of about 0.5–50 mg/kg of body weight per day. Preferably the total dosages are administered in 2–4 divided doses per day.

When administered parenterally, e.g. intravenously, the compounds are administered at a dosage range of about 0.01 to 10 mg/kg body weight in single or multiple daily doses. Of course, the dose will be regulated according to the judgment of the attending clinician depending on factors such as the degree and severity of the disease state and age and general condition of the patient being treated. The usual dosage range for the preferred compounds of this invention is an oral dose of about 75 to 1600 mg/day, preferably 600 to 800 mg/day, in 2 to 4 divided doses. This dosage regimen achieves relief of the symptoms of peptic ulcer disease and promotes the healing of gastric and/or duodenal ulcers.

To treat peptic ulcer disease, gastric and duodenal ulcers, and prevent and treat drug-induced gastric ulceration, the active compounds of this invention can be administered in unit dosage forms such as tablets, capsules, pills, powders, granules, sterile parenteral solutions or suspensions, suppositories mechanical delivery devices, e.g. transdermal, and the like. Such dosage forms are prepared according to standard techniques well-known in the art.

The following example illustrates the preparation of compounds and compositions of this invention. All temperatures are in degrees Celsius.

EXAMPLE 1

2-Methyl-9-phenyl-7H-8,9-dihydropyrano[2,3-c]imidazo-[1,2-a]pyridin-3-acetonitrile.

A. Stir a mixture of 24 g (0.13 mol) 2-methyl-8-hydroxyimidazo[1,2-a]pyridin-3-acetonitrile and 26 g (0.14 mol) N,N-dimethylmethyleneammonium iodide in 4L methylene chloride at ambient temperature for 4 days. Isolate the resulting solid by filtration, treat with 200 ml dilute ammonium hydroxide and extract continuously with methylene chloride for 4 hr. Remove the methylene chloride under reduced pressure and obtain 20 g 2-methyl-7-dimethylaminomethyl-8-hydroxyimidazo[1,2-a]-pyridin-3-acetonitrile.

B. Heat under reflux a solution of 23.7 g (0.1 mol) 2-methyl-7-dimethyl-aminomethyl-8-hydroxyimidazo[1,2-a]-pyridin-3-acetonitrile and 18.9 g (0.1 mol) 1-phenyl-1-N-morpholinoethylene in 400 ml p-dioxane in a nitrogen atmosphere for 3 hr. Upon cooling, remove the solids by filtration and concentrate the filtrate under reduced pressure. Triturate the residue with hot ethyl acetate (250 ml) and remove the solids by filtration. Dilute the ethyl acetate solution with 250 ml ether, filter and treat the filtrate with excess ethereal hydrogen chloride. Isolate the solid by filtration and wash with water (50 ml). Recrystallize from methanol and obtain 4.3 g 8-hydroxy-2-methyl-7-((3-phenyl-3-oxo)propanyl)imidazo-[1,2-a]pyridin-3-acetonitrile hydrochloride hemihyrate, m.p. 215°–220°.

C. Treat a suspension of the compound prepared in part A above, 3.5 g (0.01 mol), in ethanol (200 ml) and methylene chloride (50 ml) with 2.4 g sodium borohydride over 15 minutes. After stirring overnight, remove the volatiles under reduced pressure and treat the residue with water (125 ml) and acidify with 6N hydrochloric acid. Basify the solution to pH 8 using concentrated ammonium hydroxide and extract with methylene chloride. Remove the methylene chloride under reduced pressure and obtain the "diol" which can be used without further purification.

D. Treat a solution of 2.7 g (0.008 mol) 8-hydroxy-2-methyl-7-((3-phenyl-3-hydroxy)propanyl)imidazo[1,2-a]-pyridin-3-acetonitrile in 150 ml methylene chloride with 3 ml boron trifluoride etherate. Treat the mixture with some sand and stir at ambient temperature for 2 hr. Add an additional 3 ml boron trifluoride etherate, stir for 1 hr. and heat under reflux for 3 hr. After stirring overnight, treat the mixture with dilute ammonium hydroxide (500 ml) and methylene chloride (200 ml). Separate the methylene chloride, filter through celite and concentrate under reduced pressure to give an oil. Chromatograph on silica gel using 0.5% methanol in methylene chloride gave and obtain the title compound, m.p. 158°–161°.

Treat an etheral solution of the title compound with ethereal hydrogen chloride and obtain the hydrochloride salt of the title compound, m.p. 220°–245°.

Following the procedures of Example I using appropriate reagents, 3-Amino-2-methyl-9-phenyl-7-H-8,9-dihydropyrano[2,3-c]imidazo[1,2-a]pyridine can also be prepared:

The following formulations exemplify some of the dosage forms in which the compounds of this invention may be employed. In each the active ingredient is designated by the term "Drug" which is meant to indicate one of the following compounds:

1. 2-methyl-9-phenyl-7H-8,9-dihydropyrano[2,3-c]imidazo-[1,2-a]pyridine-3-acetonitrile hydrochloride hydrate.
2. 3-Amino-2-methyl-9-phenyl-7H-8,9-dihydropyrano[2,3-c]-imidazo[1,2-a]pyridine;
3. 2,3-Dimethyl-9-phenyl-7,8-dihydroimidazo[2,1-a]isoquinoline;
4. 3-Amino-2-methyl-9-phenyl-7,8,9,10-tetrahydroimidazo-[2,1-a]isoquinoline;
5. 2-Methyl-9-phenylmethyl-7,8-dihydroimidazo[2,1-a]-isoquinoline-3-acetonitrile.

It is contemplated, however, that each of these exemplar compounds may be replaced by equally effective quantities of other compounds within the scope of this invention. All temperatures are in degrees Celsius.

| | Formulation 1 Tablets | | |
|---|---|---|---|
| No. | Ingredient | mg/tab | mg/tab |
| 1 | Drug | 25.0 | 400.0 |
| 2 | Lactose, impalpable powder, USP | 114.0 | 241.5 |
| 3 | Corn Starch, USP | 25.0 | 50.0 |
| 4 | Corn Starch as 5% paste in distilled water | 10.0 | 35.0 |
| 5 | Corn Starch, USP | 25.0 | 50.0 |
| 6 | Magnesium Stearate, USP | 1.0 | 3.5 |
| | | 200.0 | 780.0 |

METHOD OF MANUFACTURE

Mix items Nos. 1, 2 and 3 in a suitable blender for 5 to 15 minutes. Pass through a fine screen (#40) if necessary. Reblend for 5 to 10 minutes and granulate with item No. 4. Pass the damp granulated mass through a coarse sieve (#6) using a suitable mill. Dry the damp granules at 40° to 50° overnight. Mill the dried granules using a No. 20 screen. Add item No. 5 and blend for 5 to 10 minutes. Add item No. 6 and blend further for 3 to 5 minutes. Compress the tablet mixture into tablets of an appropriate size and weight using a suitable tableting machine.

| | Formulation 2 Capsules | | |
|---|---|---|---|
| No. | Ingredient | mg/tab | mg/tab |
| 1 | Drug | 25.0 | 400.0 |
| 2 | Lactose, impalpable powder, USP | 144.0 | 191.5 |
| 3 | Corn Starch, USP | 30.0 | 105.0 |
| 4 | Magnesium Stearate, USP | 1.0 | 3.5 |
| | | 200.0 | 700.0 |

METHOD OF MANUFACTURE

Mix items Nos. 1, 2 and 3 in a suitable blender for 5 to 10 minutes. Pass through a fine screen (#40) if necessary. Reblend for 5 to 10 minutes, add item No. 4 and mix further for 3 to 50 minutes. Using a suitable machine, encapsulate the mixture into a two-piece hard gelatin capsule of appropriate size.

| | Formulation 3 Suspensions | |
|---|---|---|
| Ingredients | Formula A (mg/ml) | Formula B (mg/ml) |
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

METHOD OF MANUFACTURE

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. Dilute the suspension to final volume with purified water at 25°.

| Formulation 4 Parenteral | |
|---|---|
| | mg/ml |
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

METHOD FOR MANUFACTURE

1. Dissolve parabens in a portion (approximately 85% of the final volume) of the water for injection at 65°–70°.
2. Cool to 25°–35°. Charge and dissolve sodium bisulfite, disodium edetate and sodium sulfate.
3. Charge and dissolve the Drug.
4. Bring the solution to the final volume by adding water for injection.
5. Filter the solution through a 0.22 micron membrane and fill into appropriate containers.
6. Terminally sterilize the units by autoclaving.

| Formulation 5 Injectable Suspension | |
|---|---|
| | mg/ml |
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

METHOD OF PREPARATION

1. Dissolve parabens in a portion of water for injection at 65°–70°.
2. Cool to 25°–35°. Charge and dissolve benzyl alcohol, sodium citrate, disodium edetate, PEG 4000, povidone and sodium carboxymethylcellulose.
3. Filter the solution and sterilize by autoclaving.
4. Make a slurry of the sterile Drug and pass it through a colloid mill.
5. Mix it well with solution from Step 3 and pass it through the mill.
6. Bring the suspension to the final volume/weight and fill into sterile containers.

| | Formulation 6 Suppositories | |
|---|---|---|
| A. | Formula | mg/supp |
| | Drug | 5.0 |
| | Cocoa butter | 1995.0 |
| | | 2000.0 mg. (2.0 g.) |

PROCEDURE

1. Melt cocoa butter to about 32°–35°.
2. Blend Drug into cocoa butter until well dispersed.
3. Pour into teflon-coated mold and congeal in refrigerator. Keep in refrigerator for an appropriate length of time.
4. Remove suppositories from mold.

| B. | Formula | mg/supp |
|---|---|---|
| | Drug | 100.0 |
| | PEG 1000 | 1824.0 |
| | PEG 4000 | 76.0 |
| | | 2000.0 mg. |

| B. Formula | mg/supp |
|---|---|
| | (2.0 g.) |

PROCEDURE

1. Melt PEG 1000 and PEG 4000 in one container to 50°.
2. Add Drug to mixture. Blend until well dispersed.
3. Pour into mold and congeal in refrigerator. Keep in refrigerator for an appropriate length of time.
4. Remove suppositories from mold.

Since all the compounds within the class of compounds encompassed by this invention are not equally therapeutically potent, certain subgroups and certain specific compounds have been found to be preferred for their therapeutic utility. Preferred are those compounds wherein the tricyclic nucleus contains a dihydropyrano ring and is substituted in the 9-position by a phenyl. Still, another preferred group consists of those compounds containing a cyanomethyl, an amino or an alkyl substituent, particularly methyl, at the 2-position and a cyanomethyl, methyl or amino at the 3-position. Preferred specific compounds include those compounds of Formula I having the following substituents:

| $R_2$ | $R_3$ | X | (n) | AR |
|---|---|---|---|---|
| $CH_3$ | $CH_2CN$ | H | 0 | phenyl |
| $CH_3$ | $CH_2CN$ | H | 1 | phenyl |
| $CH_2OH$ | $CH_2CN$ | H | 1 | phenyl |
| $CH_3$ | $CH_2CN$ | H | 1 | thienyl |
| $CH_3$ | $NH_2$ | H | 1 | phenyl |
| $CH_3$ | $CH_2OH$ | H | 1 | phenyl |
| $CH_3$ | $CH_2CN$ | H | 1 | phenyl |
| $CH_3$ | $CH_2CN$ | H | 2 | phenyl |
| $CH_3$ | $CH_3$ | H | 1 | phenyl |
| $CH_3$ | $NH_2$ | H | 1 | thienyl |
| $CH_3$ | $NH_2$ | H | 2 | phenyl |
| $CH_3$ | $NH_2$ | H | 1 | phenyl |
| $CH_3$ | $NH_2$ | H | 1 | phenyl |
| $CH_3$ | $NH_2$ | H | 1 | phenyl |
| $CH_3$ | $NH_2$ | H | 1 | thienyl |
| $CH_3$ | $CH_3$ | H | 1 | phenyl |
| $CH_3$ | $CH_3$ | H | 1 | thienyl |
| $CH_3$ | $CH_2CN$ | H | 1 | phenyl |
| $CH_3$ | $CH_2CN$ | H | 1 | thienyl |
| $CH_3$ | $CH_3$ | H | 1 | phenyl |
| $CH_3$ | $CH_2CN$ | H | 1 | phenyl |

We claim:

1. A compound represented by the formula

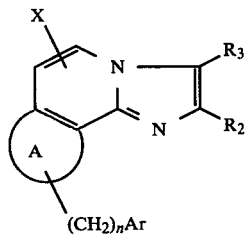

or a pharmaceutically acceptable salt thereof; wherein $R_2$ represents hydroxy, lower alkyl or hydroxyloweralkyl;

$R_3$ represents hydrogen, lower alkyl, —$CH_2CN$, hydroxyloweralkyl, —NO, —$CH_2NC$ or

wherein $R_4$ and $R_5$ are independently selected from the group consisting of hydrogen and lower alkyl;

X represents hydrogen, lower alkyl, halogen, hydroxy, lower alkoxy or trifluoromethyl;

A is a non-aromatic ring fused to the pyridine ring containing, with the carbon atoms of the pyridine ring to which it is attached, 5 or 6 ring atoms of which all are carbon or one is selected from nitrogen, sulfur or oxygen with the remaining atoms being carbon wherein the heteroatom of the 5-membered ring is at the 7 or 9 position and the heteroatom of the 6-membered ring is at the 10 position;

Ar represents phenyl, pyridyl, thienyl, imidazolyl, furanyl or X'- Y'- and Z'- substituted- phenyl wherein each of X'-, Y'- and Z'- independently is as defined for X; and n is zero, one or two.

2. A compound of claim 1 wherein ring A is dihydropyrano, $R_2$ represents hydrogen, lower alkyl with 1 to 3 carbon atoms or —$CH_2OH$;

$R_3$ represents hydrogen, lower alkyl with 1 to 3 carbon atoms, —$CH_2OH$, —$CH_2CN$ or —$NH_2$;

X represents hydrogen or methyl; and n is zero or 1.

3. A compound of claim 2 wherein —$(CH_2)_nAr$ is at the 9-position of the A ring.

4. A compound of claim 3 wherein n is zero and Ar is phenyl.

5. A compound of claim 4 wherein $R_2$ represents methyl; $R_3$ represents methyl, —$CH_2CN$ or $NH_2$; and X represents hydrogen.

6. The compound of claim 5 wherein $R_2$ is methyl and $R_3$ is acetonitrile, i.e. 2-methyl-9-phenyl-7H-8,9-dihydropyrano[2,3-c]imidazo[1,2-a]pyridine-3-acetonitrile represented by the structure

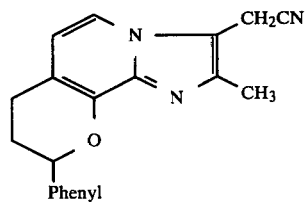

or a pharmaceutically acceptable salt thereof.

7. A compound of claim 6 wherein the pharmaceutically acceptable salt is the hydrochloride salt.

8. The compound of claim 5 wherein $R_2$ is methyl and $R_3$ is amino, i.e. 3-Amino-2-methyl-9-phenyl-7H-8,9-dihydropyrano[2,3-c]imidazo[1,2-a]pyridine represented by the structure

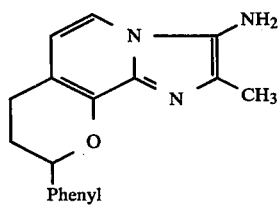

or a pharmaceutically acceptable salt thereof.

9. A compound of claim 1 where $R_2$ and $R_3$ are each methyl, the A ring is cyclohexeno and phenyl is at the 9-position, i.e. 2,3-Dimethyl-9-phenyl-7,8-dihydroimidazo-[2,1-a]isoquinoline represented by the structure

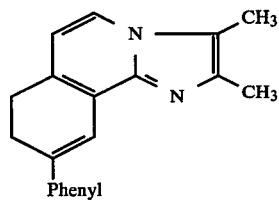

or a pharmaceutically acceptable salt thereof.

10. A compound of claim 1 wherein $R_2$ is methyl, $R_3$ is amino, the A ring is cyclohexeno and phenyl is at the 9-position, i.e. 3-Amino-2-methyl-9-phenyl-7,8,9,10-tetrahydroimidazo[2,1-a]isoquinoline represented by the structure

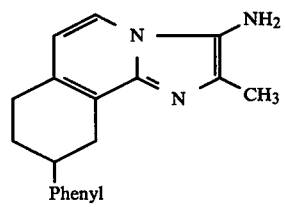

or a pharmaceutical acceptable salt thereof.

11. A compound of claim 1 wherein $R_2$ is methyl, $R_3$ is acetonitrile, the A ring is cyclohexeno and phenyl methyl is at the 9-position, i.e. 2-Methyl-9-phenylmethyl-7,8-dihydroimidazo[2,1-a]isoquinoline-3-acetonitrile represented by the structure

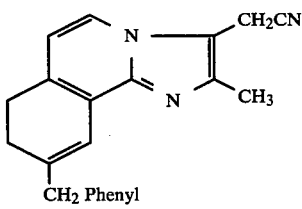

or a pharmaceutically acceptable salt thereof.

12. A pharmaceutical formulation for use in the treatment of peptic ulcer disease which comprises a compound of claim 1 in a therapeutically effective amount sufficient to alleviate the symptoms of peptic ulcer disease together with a pharmaceutically acceptable carrier.

13. A method for the treatment of the symptoms of peptic ulcer disease in mammals, which comprises administering to a mammal having peptic ulcer disease, a therapeutically effective amount of a compound of claim 1.

14. A method for the treatment of gastric ulcers in mammals which comprises administering to mammal having gastric ulcers, a therapeutically effective amount of a compound of claim 1.

15. A method for the treatment of duodenal ulcers in mammals which comprises administering to a mammal having duodenal ulcers, a therapeutically effective amount of a compound of claim 1.

16. A method for inhibiting gastrointestinal irritation and damage in mammals due to administration of drugs which induce gastrointestinal irritation and damage which comprises administering a therapeutically effective amount of a compound of claim 1 during the term said gastrointestinal irritating and damaging drug is administered for its therapeutic effect.

17. A method for the treatment of gastrointestinal damage due to stress which comprises administering to a mammal suffering from such damage, a therapeutically effective amount of a compound of claim 1.

* * * * *